(12) United States Patent
Krishnan et al.

(10) Patent No.: US 8,670,997 B2
(45) Date of Patent: Mar. 11, 2014

(54) QUALITY METRIC EXTRACTION AND EDITING FOR MEDICAL DATA

(75) Inventors: Sriram Krishnan, Exton, PA (US); William A. Landi, Devon, PA (US); Harald Steck, Phoenixville, PA (US); Romer E. Rosales, Downingtown, PA (US); Radu Stefan Niculescu, Malvern, PA (US); Farbod Rahmanian, Leesport, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1304 days.

(21) Appl. No.: 11/672,639

(22) Filed: Feb. 8, 2007

(65) Prior Publication Data

US 2007/0192143 A1    Aug. 16, 2007

Related U.S. Application Data

(60) Provisional application No. 60/771,684, filed on Feb. 9, 2006.

(51) Int. Cl.
*G06F 19/00* (2011.01)
*G06Q 50/00* (2012.01)

(52) U.S. Cl.
USPC .................................................. 705/3; 705/2

(58) Field of Classification Search
USPC ........................................................... 705/3
See application file for complete search history.

(56) References Cited

U.S. PATENT DOCUMENTS

| | | | | |
|---|---|---|---|---|
| 5,664,109 | A * | 9/1997 | Johnson et al. | 705/2 |
| 7,917,377 | B2 * | 3/2011 | Rao et al. | 705/3 |
| 2003/0120458 | A1 | 6/2003 | Rao et al. | |
| 2003/0120514 | A1 | 6/2003 | Rao et al. | |
| 2003/0125984 | A1 | 7/2003 | Rao et al. | |
| 2003/0125985 | A1 | 7/2003 | Rao et al. | |
| 2003/0130871 | A1 | 7/2003 | Rao et al. | |
| 2004/0172297 | A1 | 9/2004 | Rao et al. | |
| 2005/0216312 | A1 * | 9/2005 | Bellin et al. | 705/3 |
| 2005/0234740 | A1 | 10/2005 | Krishnan et al. | |
| 2006/0210133 | A1 | 9/2006 | Krishnan et al. | |
| 2006/0265253 | A1 | 11/2006 | Rao et al. | |

OTHER PUBLICATIONS

Cart, System Functionality, http://www.qualitynet.org/dcs/ContentServer?cid=1135267770141&pagename=QnetPublic%2FPage%2FQnetTier3&c=Page.
Cart, Recommended System Configuration, http://www.qualitynet.org/dcs/ContentServer?cid=1135267770141&pagename=QnetPublic%2FPage%2FQnetTier3&c=Page.

* cited by examiner

*Primary Examiner* — Hiep V Nguyen
(74) *Attorney, Agent, or Firm* — Joshua B Ryan

(57) ABSTRACT

Medical related quality of care information is extracted and edited for reporting. Patient records are mined. The mining may include mining unstructured data to create structured information. Measures are derived automatically from the structured information. A user may then edit the measures, data points used to derive the measures, or other quality metric based on expert review. The editing may allow for a better quality report. Tools may be provided to configure reports, allowing generation of new or different reports.

32 Claims, 7 Drawing Sheets

QUALITY METRIC EXTRACTION AND EDITING FOR MEDICAL DATA

RELATED APPLICATIONS

The present patent document claims the benefit of the filing date under 35 U.S.C. §119(e) of Provisional U.S. Patent Application Ser. No. 60/771,684, filed Feb. 9, 2006, which is hereby incorporated by reference.

FIELD

The present embodiments relate to quality metric extraction and editing, and more particularly, to systems and methods for extracting and editing information for quality of care reports.

BACKGROUND

A number of different groups require healthcare providers to extract and provide metrics on quality of care. Such groups include JCAHO, CMS, Leapfrog, and other organizations. Participation with most of these groups is voluntary, but may lead to reimbursement changes as pay-for-performance is implemented in healthcare. Furthermore, some of these metrics may become mandatory. Table 1 below is a list of common metrics:

| Initiative | Reporting Interval | Number of Indicators by Project | Population | Comparator |
|---|---|---|---|---|
| HQA (NVHRI) | Rolling Year | AMI-5 CHF-2 CAP-3 | 100% All Payer | National |
| RHQDAPU (Market Basket) | Quarterly | AMI-5 CHF-2 CAP-3 | 100% All Payer | National |
| NJ DHSS | Quarterly | AMI-9 CAP-6 | 100% All Payer | State |
| JCAHO Core Measures | Quarterly | AMI-11 CHF-7 CAP-4 | 100% All Payer | State and National |
| PRO SOW | Quarterly | AMI-8 CHF-8 CAP-4 SIP-3 | 100% Medicare | State |
| CMS Demonstration | Quarterly | AMI-9 CHF-4 CAP-7 CABG-8 Hip/ Knee-6 | 100% Payer 100% Medicare | National (292 Hospitals) |
| National Quality Forum (NQF) | Rolling Year | 27 Indicators | 100% All Payer | As Directed by Initiative |
| AHRQ (Safety Standards) | Rolling Year | 20 Indicators | 100% All Payer | Teaching Hospital >500 COTH |
| Leapfrog | Bi- annually | AMI-1 CABG-6 AAA-2 Neonatal-1 PCI-2 | Commercial/ Private Payers (Fortune 500) | State Participation (12 NJ Hospitals) |

The indicators are measures of quality based on patient treatment information. The project relates to medical conditions, such as heart attack or pneumonia. The comparator represents the scope or geographic participation with the metrics.

For healthcare providers, such as hospitals, meeting these quality reports involves laborious chart abstraction by highly qualified (and highly paid) nurses or other clinical experts. Unfortunately, many of the quality metrics (e.g., measures or facts used to determine a measure) are not stored in structured data inside a hospital database. Health care providers accumulate vast stores of clinical information. Clinical information maintained by health care organizations is usually unstructured. Since clinical information is collected to treat patients, the information may contain missing, incorrect, and inconsistent data. Often key outcomes and variables are simply not recorded.

While many health care providers maintain billing information in a relatively structured format, this type of information is limited by insurance company requirements. Billing information generally only captures information needed to process medical claims, and more importantly reflects the "billing view" of the patient, i.e., coding the bill for maximum reimbursement. As a result, billing information often contains inaccurate and missing data from a clinical point of view. Furthermore, billing codes may be incorrect.

Some systems create medical records pursuant to a predetermined structure. The health care provider interacts with the system to input patient information. The patient information is stored in a structured database. However, some physicians may prefer to include unstructured data in the patient record, or unstructured data may have been previously used for a patient.

Given the different approaches to data storage and the likely reliance on unstructured data, deriving quality metrics is expensive and cumbersome. A nurse must find patients who meet inclusion criteria set for these different quality reports, and review the reports by hand to find and enter the criteria. For example, CMS has a voluntary reporting system for several diseases, including heart failure. Every quarter, hospitals identify each heart failure patient that was treated, and fill out a form that is sent to CMS.

One computerized system, CART (CMS Abstraction and Reporting Tool) allows a user to enter in the items in an electronic form. The CART tool then verifies the results by checking for any inconsistencies. The report is sent electronically to CMS. However, a nurse or other clinical expert still manually identifies each patient who is eligible to be in the report, and then manually reviews the medical charts to extract each data point.

SUMMARY

In various embodiments, systems, methods, instructions, and computer readable media are provided for mining and editing medical related quality metric information. Patient records are mined. In one embodiment, the mining includes mining unstructured data to create structured information. Measures are derived automatically from the structured information. A user may then edit the measures, data points used to derive the measures, or other quality metric based on expert review. The editing may allow for a better quality report. Tools may be provided to configure reports, allowing generation of new or different reports.

In a first aspect, a system is provided for editing medical related quality metric information. At least one memory is operable to store at least one medical patient record. A processor is operable to extract at least a first quality metric from the at least one medical patient record, operable to receive a change request relative to the first quality metric from a user input, and operable to output the first quality metric modified as a function of the change request.

In a second aspect, a computer readable storage medium has stored therein data representing instructions executable by a programmed processor for editing medical related quality metric information. The storage medium includes instructions for mining a patient record for information related to a plurality of report values; deriving the report values from the information; displaying the report values; receiving a user edit of at least one of the report values; and generating a report as a function of the user edit and the report values.

In a third aspect, a method is provided for editing medical related quality metric information. Facts are extracted from a patient record. The facts are displayed. An edit to a first one of the facts is received. A report is generated as a function of the facts, including the edited first fact.

In a fourth aspect, a computer readable storage medium has stored therein data representing instructions executable by a programmed processor for editing medical related quality metric information. The storage medium includes instructions for providing a report template; receiving user indication of quality metrics to be included in a report; mining a patient record for information associated with the quality metrics; and generating the report with quality metric values derived from the mined information.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Quality metrics are measured automatically. If the information needed to extract the metric for a particular patient is in electronic form, the system extracts the relevant information with high accuracy. The quality metrics may be obtained for all patients or a selected sub-set of patients, not just a sampling. The extraction and resulting quality metrics may incorporate state, local, or institution-specific customizations as appropriate. Manual data collection and data entry may be avoided. By allowing editing of the quality metrics, the resulting reports may be made more accurate. By displaying supporting evidence automatically, manual review of a patient record may be limited or avoided. The report may be used for quality assurance, pay for performance, guideline adherence, and to support certification without changing the workflow of the clinicians or requiring labor-intensive manual extraction. Institutions may focus on quality issues and not on how to collect the data.

Figure 1:
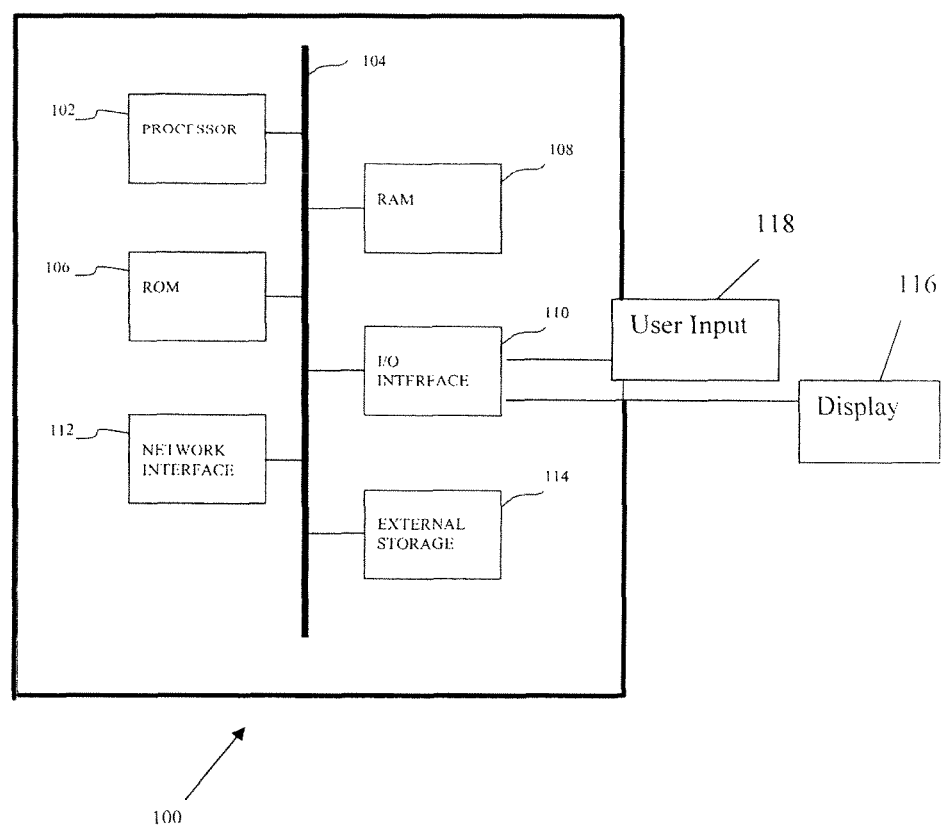
FIG. 1 is a block diagram of one embodiment of a computer processing system for extracting and editing quality metrics.

FIG. 1 is a block diagram of an example system 100 for implementing the embodiments described herein, such as editing medical related quality metric information. The systems, methods and/or computer readable media may be implemented in various forms of hardware, software, firmware, special purpose processors, or a combination thereof. Some embodiments are implemented in software as a program tangibly embodied on a program storage device. By implementing with a system or program, semi-automated workflows are provided to assist a user in generating a compliance report. The user input 118 allows editing and report generation to refine the automated output.

The system 100 is a computer, personal computer, server, PACs workstation, imaging system, medical system, network processor, or other now know or later developed processing system. The system 100 includes at least one processor (hereinafter processor) 102 operatively coupled to other components via a system bus 104. The processor 102 is implemented on a computer platform having hardware components. The other components include memories (ROM 106 and/or RAM 108), a network interface 112, an external storage 114, an input/output interface 110, a display 116, and the user input 118. Additional, different, or fewer components may be provided.

The computer platform also includes an operating system and microinstruction code. The various processes and functions described herein may be either part of the microinstruction code or part of a program (or combination thereof) which is executed via the operating system.

The user input 118 is a mouse, keyboard, track ball, touch screen, joystick, touch pad, buttons, knobs, sliders, combinations thereof, or other now known or later developed input device. The user input 118 operates as part of a user interface. For example, one or more buttons are displayed on the display 116. The user input 118 is used to control a pointer for selection and activation of the functions associated with the buttons. Alternatively, hard coded or fixed buttons may be used.

The processor 102 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 102. The processor 102 implements the program alone or is one of multiple processors in a network.

The processor 102 performs the workflows, data mining, editing, and/or other processes described herein. For example, the processor 102 is operable to extract quality metric information, provide for user editing of the quality metric information, and generate a report. Quality metric information is extracted by mining patient records. The mining may be for a patient record at one facility, but the processor 102 may link patient information to multiple facilities for more comprehensive mining of the patient records.

Example embodiments for data mining and reporting include mining from unstructured patient records using probabilities. U.S. Published Application No. 2003/0120458 discloses mining unstructured and structured information to extract structured clinical data. Missing, inconsistent or possibly incorrect information is dealt with through assignment of probability or inference. These mining techniques are used for quality adherence (U.S. Published Application No. 2003/0125985), compliance (U.S. Published Application No. 2003/0125984), clinical trial qualification (U.S. Published Application No. 2003/0130871), billing (U.S. Published Application No. 2004/0172297), and improvements (U.S. Published Application No. 2006/0265253). The disclosures of these published applications referenced above are incorporated herein by reference. Other patient data mining or mining approaches may be used, such as mining from only structured information, mining without assignment of probability, or mining without inferring for inconsistent, missing or incorrect information.

In one embodiment, compliance to a clinical guideline or other requirements is determined. For example, compliance with any of the quality metrics shown in Table 1 or other quality metrics is determined. Patient records are mined to determine compliance, such as disclosed in U.S. Published Application No. 2003/0125984, the disclosure of which is incorporated herein by reference. The compliance engine may be configured to determine compliance with clinical guidelines by comparing clinical actions with clinical guidelines as part of a knowledgebase. The clinical guidelines can relate to recommended clinical actions. The system includes an output component for outputting compliance information. The output compliance information may include quality metrics, such as report values indicating compliance with a clinical guideline or other requirement.

The processor 102 is operable to select a sub-set of the plurality of patients associated with a condition. Once a user, timing, or programming indicates a specific report should be generated, the processor 102 automatically identifies patients eligible to be included in the quality assessment report. Each quality assessment report may cover patients with one or more diseases. For example, one compliance report is the JCAHO compliance guideline for acute myocardial infraction (AMI). As another example, the CMS National Measurement Specifications have five reports covering five specific diseases: heart failure, AMI, and others.

The processor 102 automatically identifies patients who have been discharged from an institution over a user-defined period with the relevant diagnosis. Each report often has well-defined standards for how to define a patient for this report. The patient records are mined to automatically identify patients who meet these criteria. The mining is performed by the processor 102 as discussed below or in the above referenced published patent applications. Patients who should have been diagnosed but were not may be identified.

Figure 4:
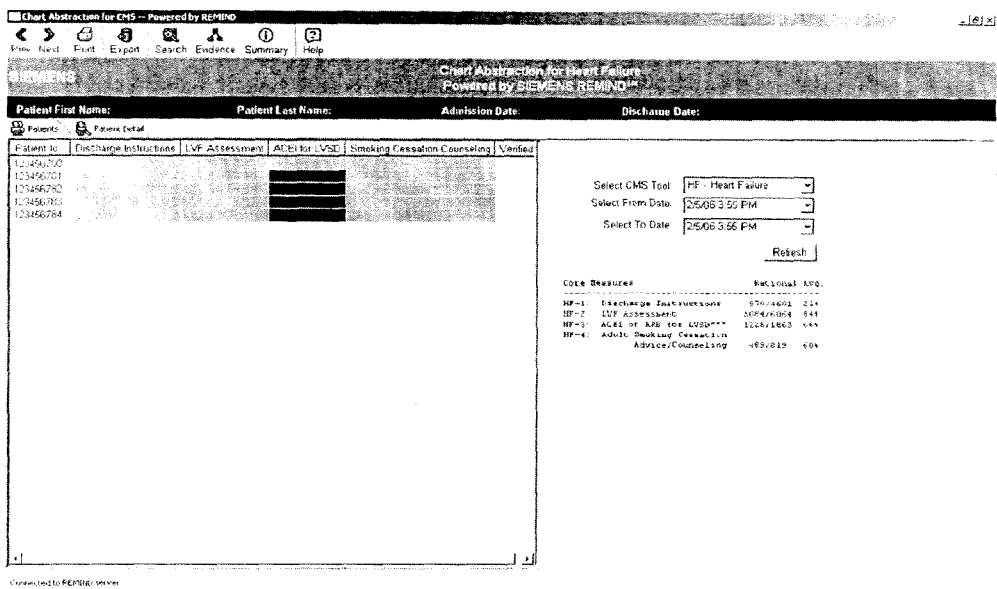
FIG. 4 shows an exemplary user interface for selecting or confirming selection of qualified patients.

FIG. 4 shows one embodiment of a user interface for an auto-population software tool. The user selects the report to be generated, such as from a drop down menu. The relevant dates are also selected. The selected report includes information to be used to determine qualification, such as key words indicating relevance to the selected report. The primary diagnosis of the patients is determined, such as heart failure in the example of FIG. 4. The patients who were discharged with a primary diagnosis of heart failure during a particular period are listed.

Once the patients are identified, compliance with a corresponding clinical guideline is determined. The selection of patients may be performed substantially simultaneously with mining quality metrics. Since similar information may be used to determine whether the patient is associated with the condition for the report and the associated measures to be included in the report, overlapping processes may be used for both selection and determining report values. FIG. 4 shows an indication as to whether the extracted information indicates if certain core measures (e.g., defined by CMS or other selected report) is met for each patient. Different, less, or additional information may be displayed.

The processor 102 is operable to extract quality metrics from available medical patient records. Quality metrics include the facts used to determine a measure or report value, measures or report values, or other information used to generate a given report. Different reports may use different measures, such as the CMS heart failure report having four measures (e.g., receipt of discharge instructions, LVF assessment, ACEI or ARB for LVSD, and adult smoking cessation). These report values or measures are extracted by identifying and extracting relevant information, such as age, sex, race, billing code, diagnosis code, discharge status, or other data points.

The quality metrics are automatically extracted for each patient in the sub-set of relevant patients. The processor 102 mines the patient records and automatically extracts the quality metrics defined by that report for. Any technique may be used for mining the patient record, such as structured data based searching. In one embodiment, the probabilistic methods, systems and/or instructions disclosed in U.S. Published Application No. 2003/0120458 are used, such as for mining from structured and unstructured patient records. The quality metrics are extracted, and the confidence associated with each extraction may also be computed and displayed.

Figure 3:
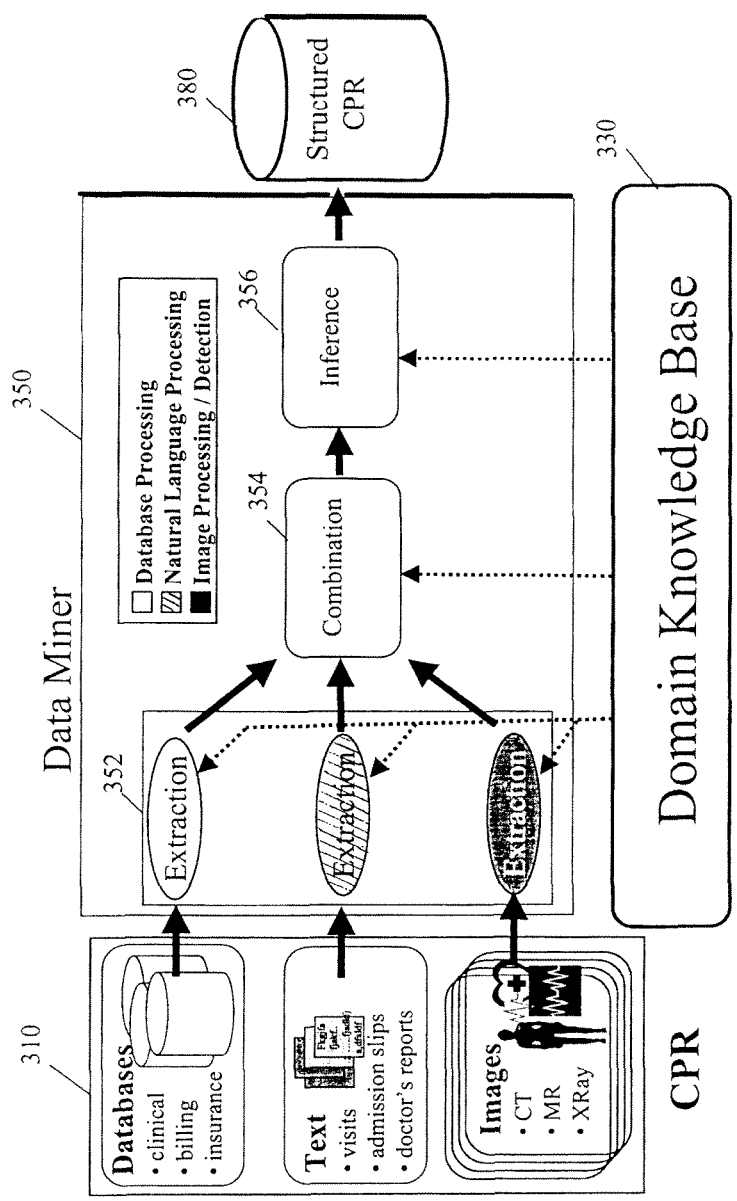
FIG. 3 shows an exemplary data mining framework for mining quality metric information.

FIG. 3 illustrates an exemplary data mining system implemented by the processor 102 for mining a patient record to create high-quality structured clinical information. The processing components of the data mining system are software, firmware, microcode, hardware, combinations thereof, or other processor based objects. The data mining system includes a data miner 350 that mines information from a computerized patient record (CPR) 310 using domain-specific knowledge contained in a knowledge base 330. The data miner 350 includes components for extracting information from the CPR 352, combining all available evidence in a principled fashion over time 354, and drawing inferences from this combination process 356. The mined information may be stored in a structured CPR 380. The architecture depicted in FIG. 3 supports plug-in modules wherein the system can be easily expanded for new data sources, diseases, and hospitals. New element extraction algorithms, element combining algorithms, and inference algorithms can be used to augment or replace existing algorithms.

The mining is performed as a function of domain knowledge. Detailed knowledge regarding the domain of interest, such as, for example, a disease of interest, guides the process to identify relevant information. This domain knowledge base 330 can come in two forms. It can be encoded as an input to the system, or as programs that produce information that can be understood by the system. For example, a clinical guideline to diagnosing a particular disease or diseases provides information relevant to the diagnosis. The clinical guideline is used as domain knowledge for the mining. Additionally or alternatively, the domain knowledge base 330 may be learned from test data as a function or not as a function of an otherwise developed clinical guideline. The learned relationships of information to a diagnosis may be a clinical guideline.

The domain-specific knowledge may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies. The domain-specific knowledge base may include synonyms, terms, or other indicators determined to be relevant to a particular condition, guideline, or influencing factors.

The information identified as relevant by the clinical guideline provides an indication of probability that a factor or item of information indicates or does not indicate a particular diagnosis. The relevance may be estimated in general, such as providing a relevance for any item of information more likely to indicate a diagnosis as 75% or other probability above 50%. The relevance may be more specific, such as assigning a probability of the item of information indicating a particular diagnosis based on clinical experience, tests, studies or machine learning. The domain knowledge indicates elements with a probability greater than a threshold value of indicating the patient state, diagnosis, desired data point, report value, or measure. Other probabilities may be associated with combinations of information.

Domain-specific knowledge for mining the data sources may include institution-specific domain knowledge. For example, information about the data available at a particular hospital, document structures at a hospital, policies of a hospital, guidelines of a hospital, and any variations associated with a hospital. The domain knowledge guides the mining, but may guide without indicating a particular item of information from a patient record.

The extraction component 352 deals with gleaning small pieces of information from each data source regarding a patient or plurality of patients. The pieces of information or elements are represented as probabilistic assertions about the patient at a particular time. Alternatively, the elements are not associated with any probability. The extraction component 352 takes information from the CPR 310 to produce probabilistic assertions (elements) about the patient that are relevant to an instant in time or period. This process is carried out with the guidance of the domain knowledge that is contained in the domain knowledge base 330. The domain knowledge for extraction is generally specific to each source, but may be generalized.

The data sources include structured and/or unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge encodes what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system. Extraction from a text source may be carried out by phrase spotting, which requires a list of rules that specify the phrases of interest and the inferences that can be drawn there from. For example, if there is a statement in a doctor's note with the words "There is evidence of metastatic cancer in the liver," then, in order to infer from this sentence that the patient has cancer, a rule directs the system to look for the phrase "metastatic cancer." If the phrase is found, an assertion that the patient has cancer with a high degree of confidence (which, in the present embodiment, translates to generate an element with name "Cancer", value "True" and confidence 0.9) is generated.

The combination component 354 combines all the elements that refer to the same variable at the same period to form one unified probabilistic assertion regarding that variable. Combination includes the process of producing a unified view of each variable at a given point in time from potentially conflicting assertions from the same/different sources. These unified probabilistic assertions are called factoids. The factoid is inferred from one or more elements. Where the different elements indicate different factoids or values for a factoid, the factoid with a sufficient (thresholded) or highest probability from the probabilistic assertions is selected. The domain knowledge base may indicate the particular elements used. Alternatively, only elements with sufficient determinative probability are used. The elements with a probability greater than a threshold of indicating a patient state (e.g., directly or indirectly as a factoid), are selected. In various embodiments, the combination is performed using domain knowledge regarding the statistics of the variables represented by the elements ("prior probabilities").

The patient state is an individual model of the state of a patient. The patient state is a collection of variables that one may care about relating to the patient, such as established by the domain knowledgebase. The information of interest may include a state sequence, i.e., the value of the patient state at different points in time during the patient's treatment.

The inference component 356 deals with the combination of these factoids, at the same point in time and/or at different points in time, to produce a coherent and concise picture of the progression of the patient's state over time. This progression of the patient's state is called a state sequence. The patient state is inferred from the factoids or elements. The patient state or states with a sufficient (thresholded), high probability or highest probability is selected as an inferred patient state or differential states.

Inference is the process of taking all the factoids and/or elements that are available about a patient and producing a composite view of the patient's progress through disease states, treatment protocols, laboratory tests, clinical action or combinations thereof. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, or other information). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer <cancer=True (probability=0.35), cancer=False (probability=0.65)> (e.g., 35% of patients have cancer). Then, this assertion is combined with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer=True (probability=0.1), cancer=unknown (probability=0.9)> and
4. <cancer=False (probability=0.4), cancer=unknown (probability=0.6)>.

In this case, we might combine these elements with the base probability of cancer <cancer=True (probability=0.35), cancer=False (probability=0.65)> to conclude, for example, that <cancer=True (prob=0.67), cancer=False (prob=0.33)>.

In alternative embodiments, specific probabilistic conclusions are determined without mining for an overall or temporal patient state. For example, the quality metrics for a report are extracted without determining a progression of conditions or other history associated with a patient.

Numerous data sources may be assessed to gather the elements, and deal with missing, incorrect, and/or inconsistent information. As an example, consider that, in determining whether a patient has diabetes, the following information might be extracted:

(a) ICD-9 billing codes for secondary diagnoses associated with diabetes;
(b) drugs administered to the patient that are associated with the treatment of diabetes (e.g., insulin);
(c) patient's lab values that are diagnostic of diabetes (e.g., two successive blood sugar readings over 250 mg/d);
(d) doctor mentions that the patient is a diabetic in the H&P (history & physical) or discharge note (free text); and
(e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. These observations (e.g., about the billing codes, the drugs, the lab tests, etc.) may be probabilistically combined to come up with a final probability of diabetes. Note that there may be information in the patient record that contradicts diabetes. For instance, the patient has some stressful episode (e.g., an operation) and his blood sugar does not go up. In another example, observations of ST-elevations in an EKG can increase confidence that the patient had a heart attack, even though the ST-elevations alone are not conclusive evidence of a heart attack.

The above examples are presented for illustrative purposes only and are not meant to be limiting. The actual manner in which elements are combined depends on the particular domain under consideration as well as the needs of the users of the system. Further, while the above discussion refers to a patient-centered approach, multiple patients may be handled simultaneously. Additionally, a learning process may be incorporated into the domain knowledge base 330 for any or all of the stages (i.e., extraction, combination, inference).

In the case of a missing information, no supporting evidence is found. The processor 102 may respond in one of two ways. The field may be left blank, or a prior probability is used to compute the most likely response. For example, one of the questions asked is whether the patient is a smoker or not. If there is no evidence provided in the patient record if the user is a smoker, then the system leaves this blank or records that the user is not a smoker, since the prior probability (based on the percentage of smokers) suggests that the patient is probably not a smoker.

The mining may be run using the Internet. The created structured clinical information may also be accessed using the Internet. Additionally, the data miner may be run as a service. For example, several hospitals may participate in the service to have their patient information mined for compliance, and this information may be stored in a data warehouse owned by the service provider. The service may be performed by a third party service provider (i.e., an entity not associated with the hospitals).

The domain knowledgebase, extractions, combinations and/or inference may be responsive or performed as a function of one or more parameter values. For example, the probabilistic assertions may ordinarily be associated with an average or mean value. However, some medical practitioners or institutions may desire that a particular element be more or less indicative of a patient state. A different probability may be associated with an element. As another example, the group of elements included in the domain knowledge base for a particular disease or clinical guideline may be different for different people or situations. The threshold for sufficiency of probability or other thresholds may be different for different people or situations.

The mining generates data points and/or report values. Once the structured CPR 380 is populated with patient information, data points are provided in a form conducive for answering questions regarding compliance, such as determining report values or measures. The structured information may include the report values in addition to data points used to derive the report values. For example, the factoids and the combined information are included as extracted or structured information.

Figure 5:
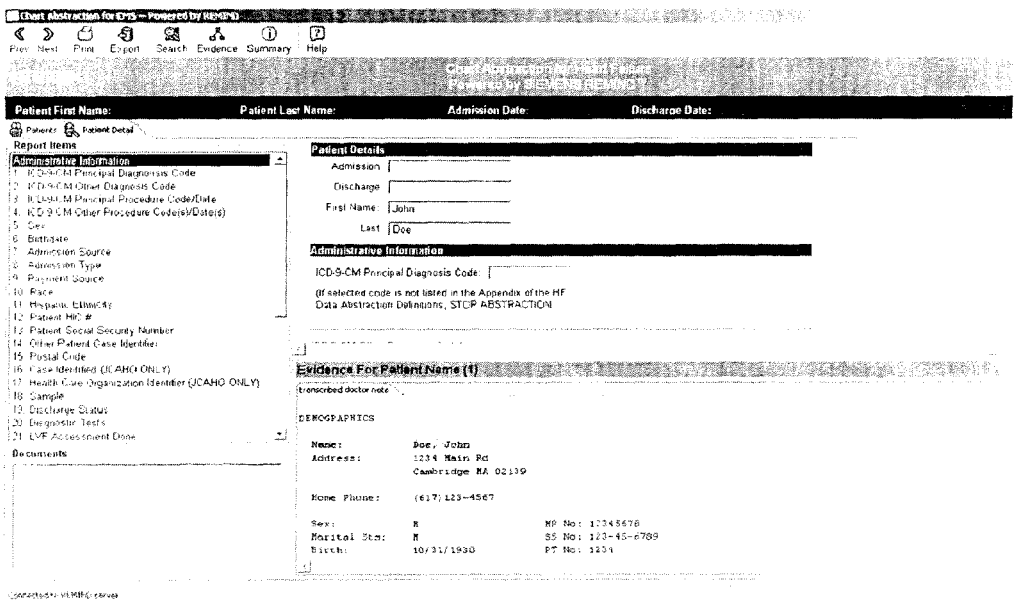
FIG. 5 shows an exemplary user interface for displaying and editing quality metric information.

The processor 102 is operable to output the quality metrics. The quality metrics are output in a report, but may be output individually. Any report format may be used. For example, FIG. 5 shows a user interface with extracted information. A list of information extracted from the patient record is shown on the left. In the right top, patient details (John Doe) extracted from the patient record are shown. The quality metrics are auto-populated.

The report is a display, such as shown in FIG. 5, a database, a spread sheet, a print-out, or other media so that the user may view the quality metrics. The quality metrics may be incorporated into a single report or a plurality of reports. Low probability, missing, contradictory, or other quality metrics of interest may be highlighted or otherwise indicated to the user. For example, a quality metric, such as an extracted data point or measure, flashes, is displayed in a different color, is bolded, is underlined, or is otherwise indicated to the user if the confidence of extraction is below a certain defined threshold (e.g. confidence below 80%).

For compliance monitoring, a statistical summary of clinical information for a plurality of patients may be output. The compliance may indicate a number, percentage, mean, median or other statistic of patients satisfying, not satisfying, or with unknown adherence to a clinical guideline. The patients associated with a particular diagnosis may be identified, such as by listing, billing code, or other input.

The processor 102 generates the report in a same format as will be used for a final version. In another embodiment, the report prior to generating a final version has a different format than the final version. Statistics or other information across the selected patients may not be provided or are provided differently. All patients or patients associated with unusual information (e.g., missing data or lower confidence) may be separately provided to the user. Patients associated with a greater deviation than the norm from some statistics may be identified. The user verifies the information on a patient-by-patient basis.

In another embodiment, the compliance information is summarized in the report. Any summary may be provided, such as a table, chart, graph or combinations thereof. For example, a pie chart for the results of compliance with a guideline is provided. This graph represents a summary statistic, which may be useful for a hospital administrator or medical professional.

The report is provided to a local or remote user for editing. Any of the quality metrics, such as the data points or the resulting measures or report values, may be edited. Some or no values may be locked from editing. The report is output before receiving any change request in order to allow professional review of the results before formal submission. In one embodiment, the output is displayed as part of a user interface allowing interaction, such as shown in FIG. 5.

To assist in editing, evidence supporting one or more quality metrics may be provided by the processor 102. For example, the user selects a quality metric. The example of FIG. 5 shows selection of patient name. In the lower right of the user interface, the evidence is provided. The evidence is a transcribed doctor's note or demographics text containing the patient's name. To aid the user, the relevant portion of the information (e.g., the name) is highlighted. This interaction or display allows a user to obtain information supporting quality metrics.

An extracted metric is automatically linked to one or more pieces of evidence. The quality metrics extracted come from the patient record. Often, the user will want to know from where the evidence for a particular extraction came. Some quality metrics may be extracted from combining information from more than one source. In this case, the evidence from different pieces of evidence can be displayed or a list of evidence sources or links created. The evidence may be a mix of evidence from structured (e.g., billing, lab results, or diagnosis codes) and unstructured (free text, or images) sources. For images, genomic/proteomic data, or other non-textual sources, special-purpose algorithms may be used to process the data, extract information, and show the evidence. For scanned documents, an OCR or handwriting-recognition algorithm may be used to convert the scanned doc into free text, after which natural language processing methods are used to identify the evidence.

Figure 6:
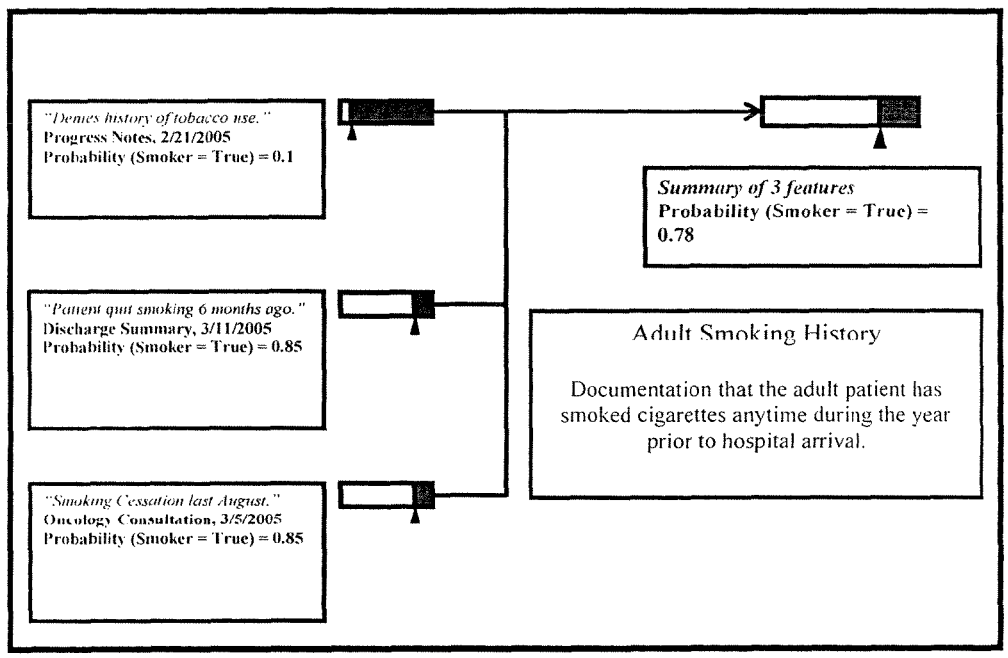
FIG. 6 shows one embodiment of a method for probabilistically determining a quality metric report value.

A user may be assisted in editing by an indication of how the processor 102 combined the different pieces of evidence to reach a conclusion. FIG. 6 shows an example embodiment of a graphical representation displayed by the processor 102 in response to user selection of a quality metric. In this example, the processor 102 extracted whether a patient has smoked in the last 12 months or not. There may be some evidence indicating that he was a smoker, and some evidence indicating that he was not a smoker. Three pieces of evidence were extracted in the example of FIG. 6 from various parts of the patient record. Note that some of these pieces are contradictory. This is common in medical records, where seemingly contradictory evidence is given. The processor 102 infers a conclusion even in the presence of contradictory evidence. In the case of multiple pieces of evidence, how the pieces of evidence are combined to reach a conclusion is shown by blocks for each piece of evidence, including associated probabilities. Links between the blocks show the relationship. The graphic is presented to the user to allow the user to understand why a particular conclusion is given.

The visual representation may have any number of inputs, outputs, nodes or links. The types of data are shown. Other information may also be shown, such as inserting actual states of the data (e.g., fever as a type of data and 101 degrees as the actual state of the fever information). The relative contribution of an input to a given output may be shown, such as colors, bold, or breadth of a link indicating a weight. The data source or sources used to determine the actual state of the data may be shown (e.g., billing record, prescription database or others). Alternatively, only the type of data and links, or other combination of information is shown.

The visual representation may be different for different patients. For example, different patients have data in different data sources. A same factoid may be derived from different locations, so the display of the data source may be different. A different set of elements may be used to infer a same or different patient state, so different elements or types of data are shown. Different actual states may be shown. Different links may exist even to reach a same conclusion or patient state. The probability associated with a patient state, element or factoid may be different, so the visual representation may also be different to reflect the probability (e.g., different color, line width, displayed percentage or other visual queue).

As another example, the level of detail may be different for different users. A visual representation for a patient may include only the elements, nodes, and links. The same patient record may be used to generate a visual representation for a physician with the relative weights and probability information. The number of elements, nodes, or links may be different.

If no evidence was found, the processor 102 gives a default value, or the value is left blank. The data sources examined (e.g. documents) may be shown so that the user can try to make a determination themselves about the result. Data sources most likely to be associated with the missing information may be shown first or provided separate from other data sources.

Evidence supporting a summary statistic quality metric may be presented. Selection of the summary statistic may result in identification of the patients resulting in the statistic being high, low, or both. For example, a user may desire to determine which patients are not being treated properly, which doctors are associated with deviations from the clinical guideline, or where documentation of proper treatment is not being entered. By grouping the patients, the user may focus on editing extracted information for patients in a particular category relative to the summary statistic.

The user selects a portion of the statistical summary. For example, the processor 102 receives an indication of a selected pie chart wedge. The user navigates to the wedge, such as selecting the wedge with a mouse and pointer of the user input 118. Other selections may be received, such as selection of a cell, row or column on a table, selection of a location along an axis of a chart or graph, or combinations thereof. Other navigation may be used, such as tabbing or depressing a particular key, to select portions of the summary.

In response to the selection, data supporting the statistical summary is output. The data is for the selected portion, or includes support for the selected portion output with but distinguished (e.g., highlighted, colored, bolded or with a different font) from other data. Another summary with more detail may be output. In one embodiment, a table listing the patients, doctors and/or other information associated with the selected statistic is output. Further quality metrics and associated evidence are output in response to selections of specifics. Specifics of the patients are output, such as outputting the data mining elements or factoids in response to selection of a patient on the list. For example, by selecting John Doe, this person's records and/or the output of the data mining is displayed as shown in FIG. 5. The supporting patient information may be sorted or arranged for ease of use, such as highlighting related information.

Other indications of supporting evidence may be provided by the processor 102. For example, the verification outputs disclosed in U.S. Published Application No. 2003/01200514, the disclosure of which is incorporated herein by reference, are used.

The user changes one or more quality metrics using the user input 118. In response, the processor 102 receives a change request relative to the quality metric from the user input 118. The change request is for a change in a quality metric, change in a probability, change in evidence used to extract a quality metric, change in the data points used for a measure, or other change. The user is able to edit any of the quality metrics extracted by the system.

The processor 102 may record an user identification associated with the change request. The user signs onto the system to make edits. Due to the sign-on, the user is identified. Alternatively, a user identification is requested in response to an edit.

The processor 102 may store an annotation received from the user input. The user annotates the change to the quality metric. The annotation may provide later justification or understanding. The annotation is saved with the change.

The processor 102 modifies one quality metric based on the edit. Other fields are updated automatically. The modification may also result in changes to other quality metrics. For example, if the user deletes a source of evidence (e.g., doctor's note) since the source was saved in a wrong patient record, data points derived from this source for other metrics are no longer appropriate. Rather than requiring manual changes to all the quality metrics, the deletion triggers a new determination without the deleted data source or other adjustment. As another example, the user changes the "smoker" quality metric from "no" to "yes," the processor also changes the "smoking cessation counseling" from "N/A" to "no" or "yes."

The edits are recorded. A record or log of the edits may be graphically displayed. Quality metrics with values different due to editing may be highlighted for later review.

The processor 102 may implement a learning function for a quality metric as a function of the change request. The processor 102 may be able to learn from editing and automatically adapt to improve future performance. In one embodiment, ycorrect is the correct value for the field in question and yprev is the value for the field before user editing. x is denoted as the context, or the evidence used to infer yprev. If the value was edited, the previous value (yprev), the current value (ycorrect), and the context or evidence used (x), with an index i is stored. Multiple changes for the same quality metric for different patients may be stored as a set i. In response to generation of a report, time or other trigger, a routine to fit or learn a function (or machine learning model) from all the edits stored is called.

To learn, a function f(yprev, x) is built with parameters q, by optimizing:

$$\text{minimize\_q Sum\_i} \|\text{ycorrect\_i} - f(\text{yprev\_i, x\_i;q})\| + R(q)$$

Where $\|z\|$ represents a given norm of the argument z, i indexes the multiple examples provided by the user editing (i.e., each user editing instance is one example i), R(q) is a regularization of the parameter q.

Another possibility is to estimate a probability distribution p(ycorrect, yprev, x;s) over random variables Ycorrect, Yprev, x, and parameter s using maximum likelihood estimation or probabilistic inference methods. In the case of maximum likelihood:

$$\text{Maximize\_s product\_i p(ycorrect\_i, yprev\_i, x\_i, s)}$$

Other functions may be used.

The editing instances, along with the context or evidence x to fit a function, are used so that, when the function f is evaluated, it produces an inference of the ycorrect value given yprev (the value initially output), x (the context or evidence), and the parameters. Other machine learning models can be used.

The learned function is used for future determination of the relevant quality metric. Values for the field in question are proposed by employing the learned function after extracting a value. The extracted value is applied to the learned function. Alternatively, the processor 102 may use this learned function to reconfigure itself and produce different (ideally more accurate) results the next time the quality metric is extracted.

After any editing, any modified quality metric and any other extracted quality metrics are output. A report is generated as a function of selections from the user input for modified quality metrics. The report is of a same or different format as output by the processor 102 for editing. For example, the same report format, but including the edits, is used to output a final report. The report includes the quality metrics for one or more patients, and/or statistical summaries associated with the quality metrics. The report may include supporting evidence, links, or citations to evidence for the quality metrics. The report may be formatted based on report formats requested by quality of care organizations, such as any of the organizations noted in Table 1. An updated quality of care report with any modified quality metrics is output for use by the health institution, certification organization, quality of care review, or other purpose.

The processor 102 outputs the report on a display, into a memory, over a network, to a printer, or in another media.

Referring to FIG. 1, the network interface 112 may be a hard-wired interface. However, in various exemplary embodiments, the network interface 112 may include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The processor 102 operates pursuant to instructions. The instructions and/or patient record for extracting and editing medical related quality metric information are stored in a computer readable memory, such as the external storage 114, ROM 106, and/or RAM 108. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method steps depicted in the accompanying figures are preferably implemented in software, the actual connections between the system components (or the process steps) may differ depending upon the manner of programming.

Figure 2:
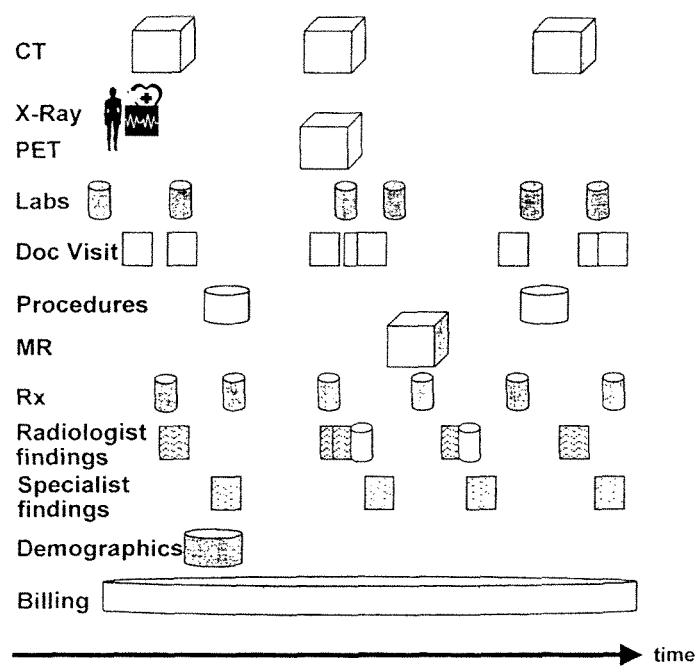
FIG. 2 shows an exemplary computerized patient record (CPR)

The same or different computer readable media may be used for the instructions and the patient record data. The patient records are stored in the external storage 114, but may be in other memories. The external storage 114 may be implemented using a database management system (DBMS) managed by the processor 102 and residing on a memory such as a hard disk, RAM, or removable media. Alternatively, the storage 114 is internal to the processor 102 (e.g. cache). The external storage 114 may be implemented on one or more additional computer systems. For example, the external storage 114 may include a data warehouse system residing on a separate computer system, a PACS system, or any other now known or later developed hospital, medical institution, medical office, testing facility, pharmacy or other medical patient record storage system. The external storage 114, an internal storage, other computer readable media, or combinations thereof store data for at least one patient record for a patient. The patient record data may be distributed among multiple storage devices as represented in FIG. 2 or in one location.

Increasingly, health care providers are employing automated techniques for information storage and retrieval. The use of a computerized patient record (CPR) to maintain patient information is one such example. As shown in FIG. 2, an exemplary CPR 200 includes information collected over the course of a patient's treatment or use of an institution. This information may include, for example, computed tomography (CT) images, X-ray images, laboratory test results, doctor progress notes, details about medical procedures, prescription drug information, radiological reports, other specialist reports, demographic information, family history, patient information, and billing (financial) information.

A CPR may include a plurality of data sources, each of which typically reflects a different aspect of a patient's care. Alternatively, the CPR is integrated into one data source. Structured data sources, such as financial, laboratory, and pharmacy databases, generally maintain patient information in database tables. Information may also be stored in unstructured data sources, such as, for example, free text, images, and waveforms. Often, key clinical findings are only stored within unstructured physician reports, annotations on images or other unstructured data source.

Referring to FIG. 1, the display 116 is a CRT, LCD, plasma, projector, monitor, printer, or other output device for showing data. The display 116 is operable to display the quality metric, patient identification, a medical patient record data supporting the quality metric, and/or other information. For example, the display 116 shows the user interfaces of FIGS. 4-6.

The display 116 may also include one or more buttons associated with macro or specific processing functions. For example, one or more "one-click" or selection-based solutions are provided. Multiple selections may be used, such as beginning extraction and report generation in response to selection of a report from a menu and relative dates. Menu or button selection may allow easy completion of the tasks required for extracting and reporting quality metrics.

Selections on the display 116 as part of the user interface may include a list of patients. Selection of a patient provides access to the metrics for the specific patient. Summary statistics or other quality metrics associated with other patients may be displayed separately or with the metrics for a specific patient.

A selection may be provided for derivation of information. For example, the user selects a button or a quality metric to show which piece(s) of information were used to infer a conclusion. FIG. 5 shows a box with highlighted evidence supporting a data point. By selecting the data point, the evidence is presented.

A selection may be provided for combination information. By selecting a quality metric derived from multiple data sources or data points, by selecting an appropriate button, or with other selection, the display 116 shows how the system combined the information to infer a conclusion. FIG. 6 shows an example result of the selection of a quality metric.

A selection may be provided for outputting a report. For example, a button is provided to exporting current report information. With one click, the user should is able to export the results to a wide variety of different sources, including data cubes, Excel sheets, text files, databases, or to a third party over the Internet, such as CMS, or to other tools, such as CART.

A selection may be provided to access to the specific metrics collected where the healthcare provider did not properly follow a particular guideline. Non-compliant cases may be identified by selecting a summary statistic, a button, or other selection. The user may more closely review the non-compliant cases.

A selection may be provided for summary statistics. For example, selecting the report and performing extraction may automatically display how the healthcare provider did on a set of quality metrics with respect to compliance. A specific button may be provided for determining the summary statistics. For example, a user edits individual patient information before selecting the summary statistic button. Comparison statistics with state, national, or other benchmarks may also be provided in response to the same selection or a different selection.

The patient data extracting, editing, report generation, with or without the user interfaces or outputs discussed above, may be associated with a healthcare workflow. For example, patient data mining is used to generate a report, and the output is used to initiate or trigger a workflow based on a particular criteria. The patient data mining may initiate the workflow without an external query. As another example, the workflow queries the patient data mining. A separate program may generate the report information from a memory of structured data. The program queries a different program for data mining to provide structured information to allow report generation. After the data mining is completed, the resulting structured information may be queried automatically to find one or more items. The workflow is a separate application that queries the results of the patient data mining and uses these results or is included as part of the data mining application. Any now known or later developed software or system providing a workflow engine may be configured to initiate a workflow based on data.

Figure 7:
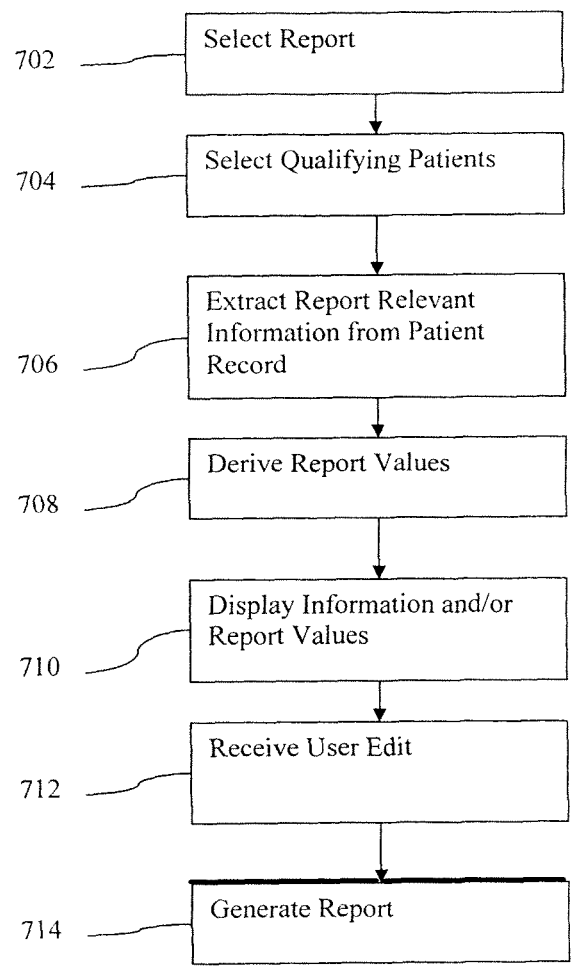
FIG. 7 shows one embodiment of a method for extracting and editing quality metrics for a report.

FIG. 7 shows one embodiment of a method for editing medical related quality metric information. The method is implemented with the system of FIG. 1 or a different system. The acts are performed in the order shown or a different order. Additional, different, or fewer acts may be provided.

In act 702, a quality of care report is selected. The user may select the report from any number of possible reports. The user may create the report. Alternatively, a processor selects the report. For example, a report is generated periodically. The report is selected for providing results or a reminder to a user. Any report may be selected, such as the CMS Heart Failure metrics or reports in Table 1. Other selections may be made for a given report, such as a date range and/or specific institution.

In act 704, qualifying patients are selected. A sub-set of all the patients of an institution is selected. The selected patients are ones diagnosed with or including an indication of the condition relevant for the report. The system automatically selects patients who meet the criteria for the report. In the CMS Heart Failure report example, the system may automatically find patients who were discharged from the hospital during the date range with a primary ICD-9 code indicating heart failure. The structured billing data is searched for patients that meet these criteria. More complicated inclusion/exclusion criteria can also be used using advanced techniques. Data mining associated with extracting quality metrics may be used to select the patients. Patients with sufficient indications of a condition whether diagnosed with the condition or not are selected. Manual selection may be used, such as a user inputting a list of patients. The user may edit by adding to or removing from the selected sub-set.

In act 706, facts are extracted from a patient record. The facts may be data points indicating a conclusion or the conclusion. The facts may or may not be accurate. The data mining described above or other data mining may be used. For example, data points are extracted by mining from structured and/or unstructured data of the patient record. For each of the patients selected, the system automatically extracts patient quality metrics as determined by the report.

Patient records are mined for information related to a plurality of report values. In some situations, the patient record may be distributed or stored at different institutions. Different institutions include doctor's offices, hospitals, health care networks, clinics, imaging facility or other medical group. The different institutions have separate patient records, but may or may not be affiliated with each other or co-owned. In order to mine the patient record, the patient records from the different institutions are linked. As an example, consider a guideline from *The Specifications Manual for National Hospital Quality Measures*. If a patient is admitted to the hospital with a primary diagnosis of heart failure, then there should be documentation of left ventricular systolic function (LVSF) assessment at any time prior to arrival or during the hospitalization. First, the hospital records are searched to find patients who were admitted with a primary diagnosis of heart failure. This can be done by searching the records (e.g., billing records and/or other data sources) of a hospital. To assess the second part, however, is a little more complicated. If a mention of LVSF assessment exists in the hospital records, as part of the history, discharge summary, or somewhere else, then the data can be assessed from the hospital data alone. Often, however, the data is not available there, but elsewhere. For example, if the patient was referred to the hospital by his cardiologist, who performed the LVSF assessment in his office the previous day, then the record of LVSF assessment is with the physician in his practice notes. If the LVSF assessment was done at one hospital, and then the patient was transferred to the current hospital, then the record of the LVSF assessment is with the previous hospital.

In act 708, report values are derived from the extracted information. Report values include the measures and/or statistics across patients to be reported. The report values are determined from one or more data points. The report values may be derived as part of the extraction. For example, the report values are derived probabilistically by combining factoids. The report values may be derived from already extracted information. Non-probabilistic derivation may be used. Report values are one type of quality metric derived for each of the patients.

In act 710, extracted and/or derived information is displayed. Factoids, data points, report values, measures, conclusions, statistics, combinations thereof, or other quality metric information is displayed. Other information may be displayed, such as evidence supporting any of the quality metrics.

The information has any format. For example, a window format of FIG. 5 is used. Other formats, such as associated with a tabbed or a fillable form may be used.

Based on extracted or derived quality metrics for each patient, summary statistics are calculated and may be displayed. The summary statistics may indicate the performance of the health institution on certain core measures. These measures can also be benchmarked against state and national standards, such as showing the benchmarks or displaying a difference.

The display may allow selection of display of different information. For example, the user of the system can select a patient, and review the quality metrics for the patient. In addition to the metrics, the system can show the user what information was used to make the decision, how this information is combined to infer an answer, and also access the documents available for the user to review. As another example, the user may select an overview or statistical summary display, such as a pie chart.

Other information may be displayed. For example, probabilities associated with the quality metrics are displayed. The probabilities may be based on domain knowledge for a specific source of evidence, the combination of probabilities, or a probability associated with conclusions, measures, or report values.

Buttons or other user interface components for simplifying navigation, extracting, editing, or other compliance reporting functions may be displayed. For example, a plurality of buttons is displayed. The buttons correspond to report related functions, such as exporting.

In act 712, an edit is received. The user enters a change to one or more of the quality metrics. For example, a fact represented by a data point is edited. As another example, an inferred conclusion or report value is edited. The user may modify any of the quality metrics based on their review of the evidence. Once the user completes with edits for a patient, the patient is marked as completed. The system can perform any consistency or other verification checks.

Information associated with an edit may be stored for later review or verification. For example, the user's reasons for making any changes are stored as an edit annotation. A user identification associated with the user edit may be stored.

In response to an edit, more than one quality metric may be changed. Another report value or quality metric depends, at least in part, on the edited quality metric. The dependent quality metrics are modified based on the modification to the base quality metric.

The edits may be stored and used to train the process. The process learns common edits in order to avoid a repetitive mistake and to improve performance. A plurality of user edits are stored and used for learning. A function or other parameter is updated as a function of the learning.

In act 714, a report is generated as a function of the user edit and the report values. After any edits are performed, the user generates a report for compliance. The quality metrics are incorporated into or are in the report. The organization desired quality metrics are provided in the report. Other quality metrics may be included. The quality metrics are based on the extracted information and any edits. The report summarizes the quality of care for patients associated with one or more conditions.

The report may be generated in response to user selection of a button or other indication of completion of edits. The report output function is performed in response to completion. The report is output to a printer, network, memory, or organization.

The report is in any desired format. For example, a format requested by a quality review organization is used. The user may print out or export the patient report with the quality metrics. Furthermore, the report or specific patient quality metrics for one or more patients may be saved. The report may be exported as either a cube text file, database file, or any other format. The user can also export the results over the Internet or other communications path to a third party, such as CMS.

Figure 8:
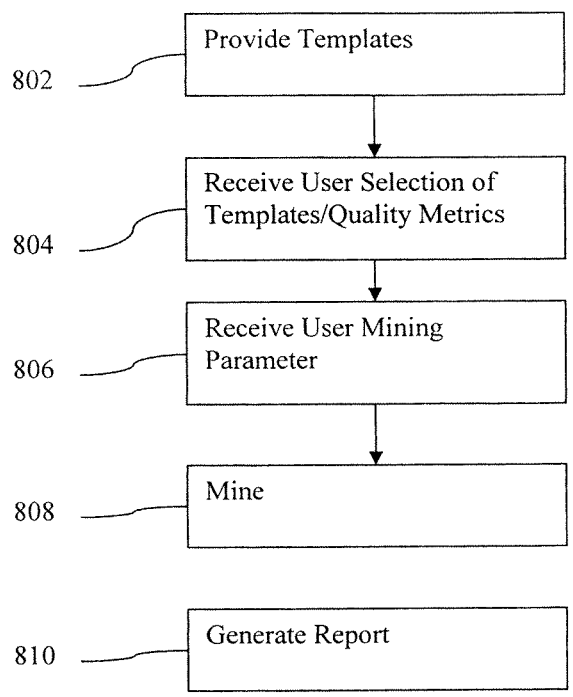
FIG. 8 shows one embodiment of a method for generating new reports.

As another example, the report is configured by the user. FIG. 8 shows one embodiment of a workflow or method for editing quality metrics. The user edits the quality metrics by creating a report, such as for a new standard. User editing of the report format may increase the usefulness of a reporting tool or engine. The user is able to define new reports using a graphical user interface. For example, new versions of the CMS reports are released almost yearly. As a result, the reports change slightly. Furthermore, new reports may be created by CMS or other organizations. It may even be the case that a particular healthcare provider wishes to create and track a unique report for their institution. The report is edited, configured, or developed by the user.

The method of FIG. 8 is performed by the system of FIG. 1 or another system. The acts are performed in the order shown or a different order. Different, additional, or fewer acts may be provided.

In act 802, a plurality of report templates are provided. The templates define different overall looks or formats for the report. Alternatively or additionally, the templates correspond to individual or groups of quality metrics. For example, the new report includes of a series of questions corresponding to quality metrics. A "report-building" engine, separate from or integrated with the mining and reporting engines, creates the report from a set of templates. One template may be provided for extracting a patient's name and primary ICD-9 code diagnosis. Another block or template may check if a particular medication is given. The user attaches these templates together to create a new report.

In act 804, user indication of quality metrics to be included in a report is received. For example, the user selects one or more templates to define a sub-set of possible quality metrics to be included in the report. The templates correspond to specific quality metrics. By selecting different templates, different quality metrics are selected for inclusion within the report. Alternatively, quality metrics are individually selected for inclusion in or addition to a selected template.

The selected quality metrics are provided for the user. The parameters used for extraction, probability, combination, inference, or combinations thereof are provided by selection of the quality metrics.

In alternative or additional act 806, the user sets one or more parameter values. The user may define one or more new quality metrics and may select or define extraction information for mining with respect to the new or a templated quality metric. For example, the user indicates data points known to the system as indicating a new quality metric. A function, such as a probability, is defined by the user for deriving the quality metric from the data points. As another example, consider the case of whether a patient has left ventricular systolic dysfunction (LVSD). This is often defined as having a measured ejection fraction (EF) <40%. There could be a template to identify if a patient has LVSD. However, another institution may want to define LVSD as having an EF <45%. In this case, the template is altered by the user to change the threshold. Another example of parameterization may be to use a different set of medications for beta-blockers.

Other variables may be user or institution specific. For example, different definitions of a primary care physician may be provided. A number of visits threshold may be used, such as visiting the same doctor 5 times indicating a primary care physician. A proximity to a patient's residence may be used. Combinations of factors may be used.

The user may select different settings for individual reports. Different users in a same institution or different institutions may use different settings. The same software or program operates differently based on receiving user input. The input may be a selection of a specific setting or may be selection of a category associated with a group of settings.

The mining, such as the extraction, the inferring, or the combining, are performed as a function of the selected threshold. By using a different upper limit of normal for the patient state, a different definition of information used in the domain knowledge or other threshold selection, the patient state or associated probability may be different. User's with different goals or standards for reports may use the same program, but with the versatility to more likely fulfill the goals or standards.

In act 808, quality metrics are extracted by mining. The extracted quality metrics correspond to the user-configured report. The user set parameters or quality metric selections define the information to be extracted. The patient record is mined based on the user-configured report.

The user-configured report is generated in act 810. The report is generated based on definition of the new report using a graphical user interface. The parameters, templates, and/or quality metrics established by the user are included in the report.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for editing medical related quality metric information, the system comprising:
 a user input device;
 at least one memory operable to store at least one medical patient record; and
 a processor configured to:
  extract at least a first quality metric from the at least one medical patient record, the first quality metric being a value indicating a quality of care related to a guideline or requirement and the first quality metric calculated from patient treatment information in the at least one medical patient record, the patient treatment information comprising a fact, inferred conclusion, or report value for a patient based on the at least one medical patient record;

receive a change request relative to the first quality metric from the user input device, the change request being for editing the patient treatment information in the at least one medical patient record used to determine the first quality metric;

change the fact, inferred conclusion, or report value to a different fact, different conclusion, or different report value in the at least one medical patient record for the editing; and output the first quality metric modified as a function of the different fact, different conclusion, or different report value.

2. The system of claim 1 wherein the processor is configured to output the first quality metric in a quality of care report before receiving the change request, and is configured to output an updated quality of care report with the modified first quality metric.

3. The system of claim 1 wherein the processor is configured to output data, from the at least one medical patient record, supporting the first quality metric.

4. The system of claim 1 wherein the processor is configured to record a user identification associated with the change request.

5. The system of claim 1 wherein the processor is configured to store an annotation received from the user input device, the annotation being for the change request.

6. The system of claim 1 wherein the processor is configured to modify a second quality metric as a function of the change request for the first quality metric.

7. The system of claim 1 wherein the processor is configured to implement a learning function for the first quality metric as a function of the change request.

8. The system of claim 1 wherein the processor is configured to generate a report as a function of selections from the user input device, the first quality metric output in the report.

9. The system of claim 1 wherein the at least one memory is configured to store at least part of the at least one medical patient record as unstructured data, and wherein the processor is configured to extract from, at least in part, the unstructured data, the extraction being probabilistic.

10. The system of claim 1 wherein the at least one memory is operable to store medical patient records for a plurality of patients, and wherein the processor is configured to select a sub-set of the plurality of patients associated with a condition, configured to extract a plurality of quality metrics for each patient of the sub-set, the plurality of quality metrics including the first quality metric, and configured to generate a report as a function of the plurality of quality metrics.

11. The system of claim 1 further comprising:
a display operable to display the quality metric, patient identification, a medical patient record data supporting the quality metric, and a plurality of buttons associated with processor functions;
wherein the user input device is operable to select the buttons.

12. In a non-transitory computer readable storage medium having stored therein data representing instructions executable by a programmed processor for editing medical related quality metric information, the storage medium comprising instructions for:

mining a patient record for patient treatment information related to a plurality of report values, the report values being metrics indicating quality of care related to a guideline or requirement;

deriving the report values from the patient treatment information;

displaying the report values for a patient at a given time;

receiving edit information from a user, the edit information being for editing at least one of a plurality of supporting data values, a relationship between the supporting data values, or both for the at least one of the report values;

changing the at least one of the data values, the relationship, or both based on the edit information, the data values and relationship between the supporting data values representing a state of the patient as indicated by the patient record such that the changing reflects a different state of the patient at the given time; and generating a report as a function of the changed at least one of the data values, the changed relationship, or both and the report values.

13. The instructions of claim 12 wherein mining comprises mining for data points, and wherein deriving comprises determining each of the report values from a plurality of the data points.

14. The instructions of claim 12 wherein displaying comprises displaying the report values and data, from the patient record, supporting the report value.

15. The instructions of claim 12 further comprising:
storing a user identification associated with the user edit information.

16. The instructions of claim 12 further comprising:
storing an annotation for the user edit information.

17. The instructions of claim 12 wherein the user edit information is of a first report value;
further comprising:
modifying a second report value in response to the user edit information of the first report value.

18. The instructions of claim 12 further comprising:
storing a plurality of user edits;
machine-learning from the user edits; and
updating a function for the deriving as a function of the learning.

19. The instructions of claim 12 wherein mining comprises mining at least some of the information from unstructured data, wherein deriving comprises probabilistically deriving the report values, and wherein displaying comprises displaying probabilities associated with the report values.

20. The instructions of claim 12 wherein mining comprises mining a plurality of patient records for a plurality of patients, including the patient record;
further comprising:
selecting a sub-set of the plurality of patients, the sub-set comprising patients associated with a condition relevant to the report;
wherein deriving comprises deriving for each of the patients; and
wherein generating comprises generating the report summarizing quality of care for the patients associated with the condition.

21. The instructions of claim 12 wherein displaying comprises displaying a plurality of buttons associated with report related functions, and wherein receiving comprises receiving user selection of one of the buttons;
further comprising:
performing the report related function associated with the one of the buttons.

22. A method for editing medical related quality metric information, the method comprising:
- extracting, by a processor, facts about a patient from a patient record, the facts representing characteristics of the patient at a given time and reflected in the patient record;
- displaying, on a display device, the facts;
- receiving, by the processor, an edit to a first one of the facts, the edit being a change of the first one of the facts from a first value to be a different value, the first value and the different value representing one of the characteristics of the patient at the same given time;
- changing, by the processor, the first one of the facts in the patient record based on the edit; and
- generating, by the processor, a report for at least one quality value calculated from the facts, the generating being as a function of the facts, including the edited first fact.

23. The method of claim 22 further comprising:
- displaying evidence from the patient record supporting the first fact.

24. The method of claim 22 wherein extracting comprises extracting from structured and unstructured data of the patient record.

25. The method of claim 22 wherein extracting comprises probabilistically determining the first fact from data of the patient record associated with the first fact.

26. The method of claim 22 wherein displaying comprises displaying an input associated with the first fact, and wherein receiving the edit comprises receiving an entry in the input.

27. The method of claim 22 wherein generating the report comprises generating the report as a function of a user configuration of the report.

28. In a non-transitory computer readable storage medium having stored therein data representing instructions executable by a programmed processor for editing medical related quality metric information, the storage medium comprising instructions for:
- providing a report template;
- receiving user indication of a plurality of different quality metrics to be included in one report, the different quality metrics indicating quality of care related to a guideline or requirement;
- selecting qualifying patients separately from the receiving of the user indication of the plurality of different quality metrics to be included in the one report;
- mining a patient record for information associated with the user-indicated quality metrics to be included in the report, the mining extracting the information from the patient record relevant to the different quality metrics received as the user indication; and
- generating the report with quality metric values derived from the mined information.

29. The instructions of claim 28 further comprising:
- receiving a user edit of a first one of the quality metric values;
- wherein generating comprises generating the report with an edited quality metric value.

30. The instructions of claim 28 wherein providing the report template comprises providing a plurality of templates associated with different quality metrics, wherein receiving user indication comprises receiving user selection of a sub-set of the plurality of templates, and wherein generating comprises generating the report as a function of the sub-set of templates.

31. The instructions of claim 28 further comprising:
- receiving a user selected parameter value;
- wherein mining comprises mining as a function of the user selected parameter value.

32. The instructions of claim 28 wherein mining comprises mining from structured and unstructured information; and further comprising:
- deriving the quality metric values as a function of probabilities associated with the information.

\* \* \* \* \*